United States Patent [19]

Pfrommer

[11] 4,401,492
[45] Aug. 30, 1983

[54] BREAST PROSTHESIS AND METHOD OF MAKING THE SAME

[76] Inventor: Arthur M. Pfrommer, 1711 Maryland Ave., Croydon, Pa. 19020

[21] Appl. No.: 395,577

[22] Filed: Jul. 6, 1982

Related U.S. Application Data

[63] Continuation of Ser. No. 139,024, Apr. 10, 1980, abandoned.

[51] Int. Cl.³ .................................................. A61F 1/24
[52] U.S. Cl. ............................................ 156/61; 3/36; 128/481; 156/145; 156/242; 156/249; 156/253; 156/280; 156/307.1; 264/4; 264/222; 264/227; 264/DIG. 30; 427/2; 428/16
[58] Field of Search ................. 156/61, 249, 145, 253, 156/242, 280, 307.1; 427/2; 428/16; 249/55; 264/4, DIG. 30, 222, 227; 3/36; 2/267; 128/481

[56] References Cited

U.S. PATENT DOCUMENTS

| | | | |
|---|---|---|---|
| 1,713,751 | 5/1929 | Sorogi et al. | 156/61 |
| 2,543,499 | 2/1951 | Kausch | 3/36 |
| 3,293,663 | 12/1966 | Cronin | 3/36 |
| 3,811,133 | 5/1974 | Harris | 264/222 |
| 4,086,666 | 5/1978 | Vaskys et al. | 3/36 |
| 4,125,117 | 11/1978 | Lee | 128/481 |

*Primary Examiner*—John J. Gallagher
*Attorney, Agent, or Firm*—Holman & Stern

[57] ABSTRACT

A method of making a mandrel for a breast prosthesis in which a negative cast is formed of the wearer's remaining breast and the area of the missing breast. A positive cast is formed of the negative cast and a model is made of the missing breast. A flexible mold is formed over the modeled breast and a portion of the positive cast. The flexible mold together with the molded breast are removed from the positive cast. An additional flexible mold is formed over the rear of the modeled breast to form a rear wall. The rear wall is removed and the modeled breast is discarded. The forward and rear walls are secured together to form a cavity. Fiberglass resin fill is inserted into the cavity and the resin is cured until it hardens to form the mandrel.

12 Claims, 10 Drawing Figures

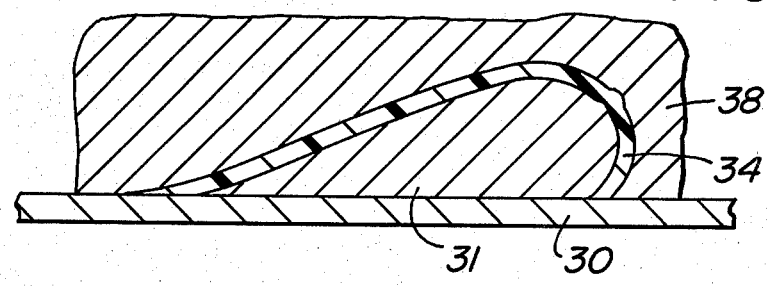
FIG. 4
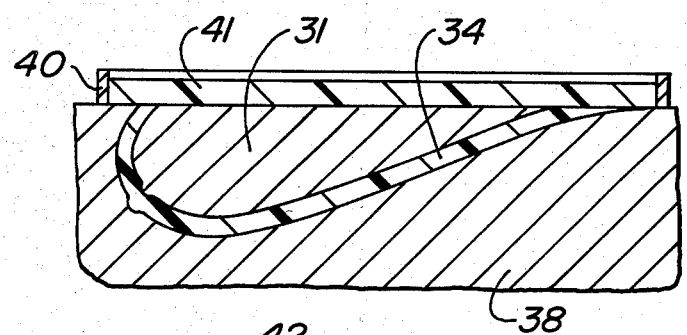
FIG. 5
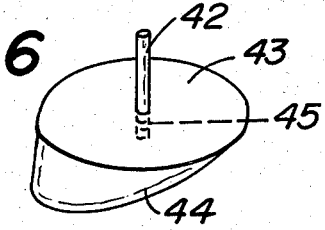
FIG. 6
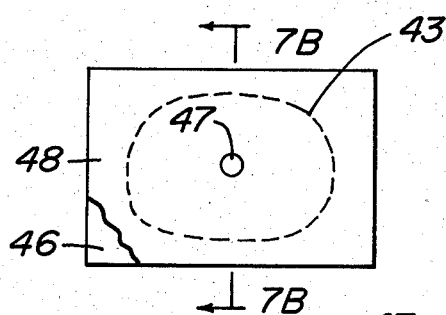
FIG. 7A
FIG. 7B
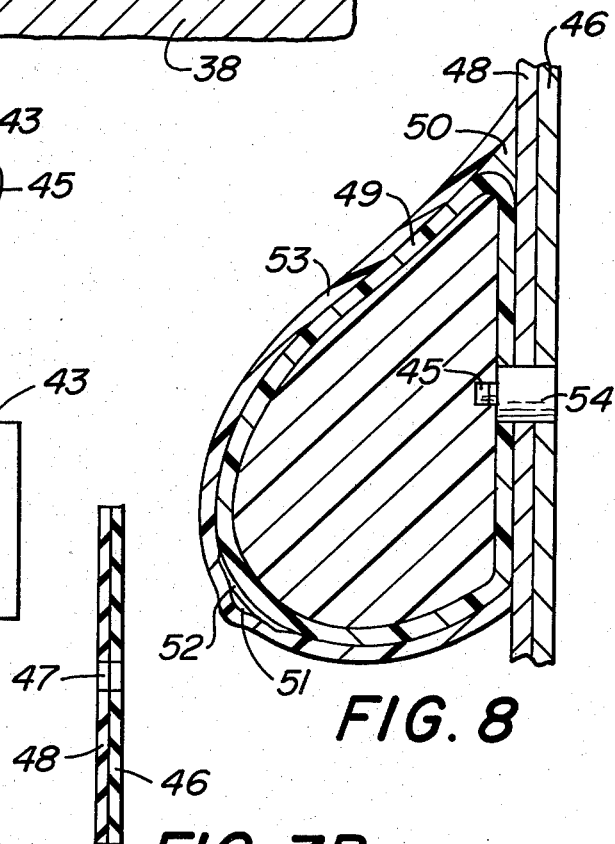
FIG. 8

BREAST PROSTHESIS AND METHOD OF MAKING THE SAME

This is a continuation of application Ser. No. 06/139,024, filed Apr. 10, 1980, now abandoned.

BACKGROUND OF THE INVENTION

A. Field of Invention

This invention relates to the field of art of breast prostheses.

B. Background Art

Prosthetic breasts have been well known for use after mastectomy operations. However, these prior devices have left much to be desired in wearing comfort as well as an exact simulation of the removed breast, the area around the breast and the muscles under the arm in a radical mastectomy. Examples of some of the prior art can be seen in U.S. Pat. Nos. 2,482,297; 2,580,264; 2,752,602; 2,814,808; 2,851,692; 2,867,818; 3,196,464; 3,619,819; 3,811,133 and 4,086,666.

One objection to prior devices has been in inability to duplicate the skin-tones of the natural breast and the color-action of the nipple and areola. The coloration has been provided on the surface of the prosthesis, thus deteriorating with usage.

Another objection to prior devices has been in inability to duplicate a smooth sloping curvature between the chest wall and the protruding natural breast. Prior devices have had a gap between the chest wall and the forward wall of the prosthesis, or have had an unnatural looking material placed in the gap. This has caused embarrassment to the wearer, especially when wearing a low-cut dress.

Prior devices have also been limited in their ability to duplicae appearance of the missing breast. Prior devices have had their outer skin take on the shapes of various available mandrels. These mandrels have been made from molds of typical sized breasts, none of which were exact duplicates of the wearer's missing breast. Due to the expense of making customized mandrels, the wearer had to settle for a breast which was only a close facsimile of her missing breast.

Still an additional objection to prior devices has been in discomfort to the wearer. These prior devices have deteriorated during use and have caused irritation and general discomfort to the wearer. Consequently, they could not be comfortably worn for an indefinite length of time without irritation.

It is the object of this invention to provide a method of making an artificial breast so that it will have the exact shape of the wearer's missing breast, will have the exact feel, color and skin tone of the wearer's natural breast, will maintain its appearance without deteriorating with usage, and will feel comfortable to the wearer over a substantially indefinite length of time.

SUMMARY OF THE INVENTION

A method of making a breast prosthesis comprises the steps of forming a negative cast of the wearer's remaining breast and the area of the missing breast. A positive cast is formed of the negative cast and a model is made of the missing breast. A flexible mold is formed over the modeled breast and a portion of the positive cast. The flexible mold and the modeled breast are removed together and turned over, with the back of the modeled breast facing up. An additional flexible mold is formed over the back of the modeled breast to form a rear wall of the prosthesis. The new wall is removed and the modeled breast is discarded. The forward and rear walls are secured together and fiberglass resin fill is inserted into the interior space between the rear and forward walls to form a mandrel. The mandrel is then removed from the flexible mold, sanded, and dipped into a liquid dispersion of silicone to form a skin surrounding the mandrel. After curing the skin, a flexible heat resistant backing sheet is secured to the mandrel to form a rear wall. The form is again cured. Colorant is applied to the skin, and nipple and areola are modeled onto it. Filler is added between the edge of the skin and the backing to simulate the smooth surface curvature between the wearer's chest wall and breast. The form is dipped into a clear liquid dispersion of silicone to form a second skin surrounding the first skin. The form is again cured. An opening is cut through rear of the backing sheet and the form is peeled from the mandrel. The opening is sealed and a gel fill is injected into the interior space.

BRIEF DESCRIPTION OF DRAWINGS

FIG. 4 is a cross sectional view of the clay modeled breast surrounded by a rubber mold and a plastic holding cup;

FIG. 5 is a cross sectional view of the clay modeled breast turned upside down, with a mold of the breast's backwall on top;

FIG. 6 is a perspective view of the mandrel used for making the prosthesis, with a rod screwed into the mandrel;

FIGS. 7A-B are a top view and a side view of the sheets used to provide a backwall for the prosthesis during its construction; and FIG. 8 is a cross sectional view of the prosthesis taken at a step in the process before the mandrel is removed.

DETAILED DESCRIPTION

Figure 1:
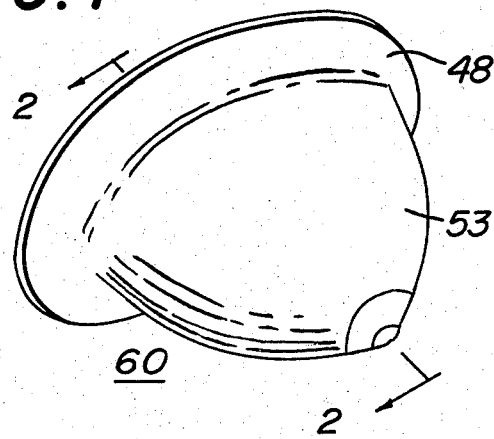
FIG. 1 is a perspective view of the forward wall of the completed prosthesis.
Figure 2:
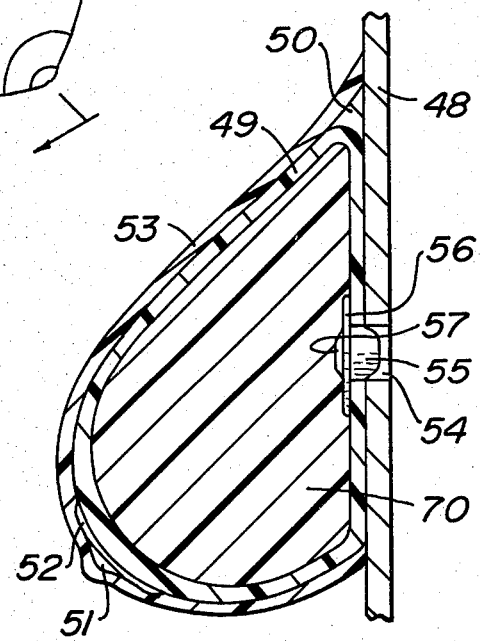
FIG. 2 is a cross sectional view of the prosthesis, filled with gel after completion.

Referring to FIGS. 1 and 2, there is shown a breast prosthesis 60 which has been made by the method steps later described in detail with respect to FIGS. 3A-8.

Prosthesis 60 has a rear or body wall 48 which is effective to lock the prosthesis to the body and eliminate slipping and sliding which is particularly a problem when the wearer is very active. Specifically, rear or body wall 48 of prosthesis 60 is contoured as a result of the described molding process exactly to the area from which a breast has been removed. As a result of this exact contour, prosthesis 60 is maintained and locked in position whether the wearer is wearing a bra or not.

Further, rear wall 48 has an opening 54 as shown in FIG. 2, which has been sealed with layers or rubber 55 and 56 and with buttom 57. The process of making the seal will be described in detail later. Button 57 acts as a plug to prevent silicone gel fill 70 from escaping containment within forward wall 53 and rear wall 48. Also, button 57 permits the initial insertion of silicone gel fill 70.

The outer or forward resilient wall of prosthesis 60 is comprised of two skins: first skin 49 and second skin 53. The process of making both skins will be described later. Skin 49 is color matched to the skin color of the wearer, and has nipple 51 and areola 52 constructed on it to match those of the wearer. Second skin 53 is transparent and colorless. Consequently, the skin colors painted onto skin 49, nipple 51 and areola 52 show through second skin 53. The colors appear as though they were placed onto second skin 53. Providing second skin 53 seals the skin colors and prevents nipple 51 and areola 52 from shifting or changing their colors. Thus, the skin appearance of breast prosthesis 60 remains as originally designed for a substantially indefinite length of time. Furthermore, second skin 53 adds strength to first skin 49, both increasing the longevity of prosthesis 60.

First skin 49 and second skin 53 have the same feel as the skin of the wearer and substantially the same softness since it is made of silicone rubber which has the same texture, softness and resiliency as a real breast. In addition, fill 70 of the prosthesis is silicone gel which provides movement throughout the prosthesis as close as possible to a normal breast. In this way there is provided a breast prosthesis which comes as close as possible to the removed breast in color, softness, contour and movement. In addition, prosthesis 60 is effectively locked in place due to the contour of rear wall 48.

The following is a series of method steps in the method of making a prosthesis 60.

STEP 1

Figure 3A:
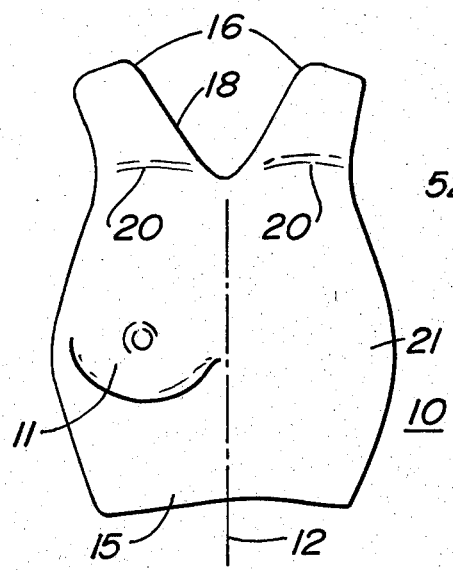
FIGS. 3A-B illustrate perspective views of a negative and a positive body cast of the wearer's body.

As shown in FIG. 3A, a waste mold is cast of the woman's body to form a negative body cast 10. The casting is done in pottery plaster of paris mixed with water and reinforced with fiberglass in conventional manner. Body cast 10 extends from the waist 15 to shoulders 16 around neck 18 and includes clavicle 20. Cast 10 includes the entire area around missing breast 21 together with remaining breast 11 (without bra) and under the arm adjacent to the missing breast. Line 12 indicates an impression of lipstick mark which has been drawn on the woman's body to indicate the center line.

STEP 2

Figure 3B:
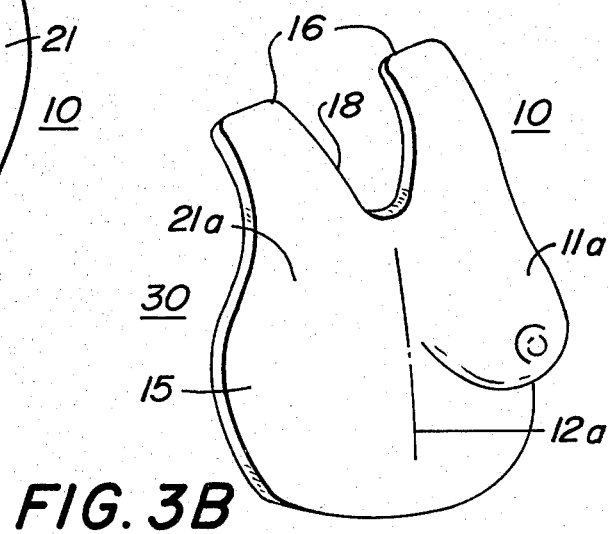

A positive body cast 30 is made of negative body cast 10. This positive body cast is also made of pottery plaster of paris reinforced with fiberglass. In conventional manner, in the waste mold process, casts 10 and 30 may be separated by sodium silicate or water glass. Thereafter, cast 10 is chipped off and the remaining cast becomes a positive body cast 30, as shown in FIG. 3B having a positive impression 11a of breast 11 and positive impression 21a of missing breast 21. Positive impression 12a of lipstick mark 12 also appears on positive body cast 30.

STEP 3

The missing breast is then modeled in clay in a manner so that it matches breast 11a. The modeling is done by a sculptor on top of area 21a and is done by eye. The sculptor attempts to match breast 11a so that modeled breast 31, FIG. 4, is an almost exact copy of the missing breast based upon the sculptor's impression of positive cast breast 11a. Since cast 10 has been made without a bra, it will be understood that modeled breast 31 is being modeled to hang naturally without a bra.

STEP 4

A silicone rubber model 34 is then formed over modeled breast 31 on cast 30 to cover all of effective area 21a. Further, mold 34 may extend in particular examples, all the way up to the shoulder in order to blend the resultant prosthesis 60 onto the body of the wearer. The silicon rubber may be Dow Corning "SILASTIC G" type silicon rubber which is relatively slow setting. The thickness of mold 34 may be about ⅛ inch thick.

STEP 5

A support casting 38 is made in conventional manner of plaster of paris to cover rubber mold 34 and may be approximately ½ to ¼ inch thick. As shown in FIG. 4, support casting 38 is flattened on the top for reason that will become apparent later. Support casting 38 is permitted to harden.

STEP 6

Support casting 38, silicon rubber 34 and clay modeled breast 31 are removed together from cast 30, and turned concave side up. Thus, support casting 38 is on the bottom, as shown in FIG. 5. Additional clay is taken and retaining wall 40 is constructed around the perimeter of plaster holding cup 38; retaining wall 40 is constructed to be approximately ¾ inch high. A conventional release agent is sprayed onto clay 31, silicon rubber 34 and plaster holding cup 38, within the perimeter of retaining wall 40. Additional silicon rubber, such as "SILASTIC G" type silicon, is poured into the area within wall 40. In this manner, there is formed back wall 41 which conforms to the woman's body.

STEP 7

Back wall 41 is removed and clay modeled breast 31 is lifted from silicon rubber 34. Back wall 41 is fitted back onto silicon rubber 34. Thus, there is formed a cavity which conforms to the area removed by the surgeon; back wall 41 conforms to the woman's back part of the breast and forward wall 34 conforms to the woman's front part of the breast. This cavity is filled with a fiberglass reinforced resin and permitted to cure. The fiberglass reinforced resin forms a mandrel, as shown in FIG. 6. Mandrel 44 is removed from silicon rubber 34 and 41. Mandrel 44 is sanded and polished until it has a glass appearing finish.

It will be understood that mandrel 44 is made from fiberglass reinforced resin which is of the conventional type and requires a catalyst to harden. The fiberglass reinforced resin is of the type suitable for use with car body repairs and is, therefore, easily sandable to form a smooth and shiny finish. For example, the fiberglass reinforced resin may be fiberglass reinforced resin No. 2595 made by Bond-Tite Division, Oatey Company, Cleveland, Ohio.

It will also be understood that the mandrel is selected of material that can hold its shape while being subjected to heat. It is not, however, necessary that the mandrel be able to survive many heatings, since it will normally be subjected to only two heat cycles. Since the mandrel only needs to withstand two heat cycles, it is not necessary that it be made of expensive material such as aluminum. Consequently, this method permits selection of inexpensive material for the mandrel, allowing a custom designed breast prosthesis for each wearer.

STEP 8

As shown in FIG. 6, a hole is drilled into mandrel 44 by way of rear surface 43. Rod 42, approximately 4 inches in length, is taken and threaded at one end, as shown. Threaded end of rod 42 is then screwed into the mandrel. It will be understood that rod 42 may be attached to a metal bar to provide convenient means for holding mandrel 44. Mandrel 44, held by rod 42, is taken into the dipping room and immersed into a liquid dispersion made from silicone. The silicone dispersion is flesh colored and is of such material as GE SE4-552C or GE SE4-552K. The mandrel is dipped severl times into the liquid to form first skin 49, shown in FIG. 8. The number of dips is dependent on the size of the mandrel; the larger the mandrel, the more are the number of dips that are required. Typically, 7 to 12 dips are required.

To product is then taken to the oven for curing. It is cured at 300° F. for approximately one hour.

STEP 9

Mandrel 44 is removed from the oven and rear of mandrel 43 is measured horizontally and vertically. Approximately 4 inches are added to these measurements. A rectangular sheet of Kodel 46 or other heat resistant polyester sheeting material is cut, as shown in FIG. 7A, to conform to both the original measurements of rear of mandrel 43 plus the added 4 inches. A calender is prepared with catalized raw rubber to a thickness of 25 mils. Kodel sheet 46 is then run through the calender in conventional manner, and coated with uncured rubber sheet 48, shown in FIG. 7B.

Hole 47 is punched through the center of Kodel sheet 46 and raw rubber 48. Hole 47 enables Kodel 46 and rubber 48 to fit over the previously placed rod 42 in mandrel 44. Raw rubber 48 is pressed against the back of first skin 49, as shown in FIG. 8, causing it to adhere. The product is then placed in an oven at 300° F. for approximately 30 minutes. This causes a vulcanizing action that makes a permanent bond between raw rubber 48 and first skin 49.

It will be understood that vulcanization is preferred over simple gluing because of the added strength. Also, Kodel is preferred, not only due to its heat resistant characteristics, but is also holds the shape of the backing in a rigid position and will not collapse when it comes in contact with the heat.

STEP 10

After cooling, rear wall 48 and first skin 49 is ready for aesthetic touch-ups. To simulate smooth curvature of the area between the woman's chest and the top of her breast, silicone rubber sealant 50, as shown in FIG. 8, is applied in conventional manner to fill in the gap between the top edge of first skin 49 and backwall 48. Sealant 50 is manually shaped to form a smooth transition from backwall 48 down to first skin 49. Sealant 50 may be made from Dow Corning 732 or SWS RTV Silicone Rubber 951.

Backwall 48, sealant 50 and first skin 49 are artiscally sprayed with coatings of silicone, which are colored to resemble skin tone of the wearer. In addition, silicone rubber tinted to the color of veins are painted onto first skin 49. The sculptor also creates nipple 51 and areola 52. Thereafter, colored silicone rubber is painted onto first skin 49 in area of the nipple and areola to simulate coloring of the wearer. This painting material is in a semi-cured state, and is composed of silicone rubber sealant mixed with silicone color, such as silicone color manufactured by the Ferro Co. of Cleveland, O.

STEP 11

The form is again taken into the dipping room and immersed in a clear liquid dispersion of silicone rubber. The form may be dipped three or more times so that it is sufficiently thick to maintain its shape. Thereafter, the form is cured in an oven at approximately 300° F. and for approximately one hour. This process yields second skin 53 shown in FIG. 8.

In this manner, the color of the form is permanently locked in. Further, by using a clear dispersion, the color is transparent to second skin 53 and appears as if it is on the surface, whereas in actuality it has three or more coats of silicone on top of it.

STEP 12

Mandrel 44 is now ready to be removed from the form. A one-inch diameter hole 54 is made through backwalls 46 and 48 and through first skin 49, as shown in FIG. 8. It will be understood that hole 54 is made by simply widening hole 47, which was cut to permit mandrel rod 42 to fit through Kodel backing 46.

Mandrel 44 is removed from the form by stretching the silicone rubber skins over mandrel 44 in the same manner as one would remove rubber gloves from a hand. The form is tested for any holes, using a high intensity light.

Kodel backing 46 is also removed at this stage. It will be understood that Kodel backing 46 must not be removed until second skin 53 and rear wall 48 have been cured (Step 11). Kodel backing 46 provides support to the form so that the form will retain its shape. After curing has occurred, rear wall 48 and second skin 53 will hold their shape without Kodel backing 46. Rear wall 48 is sufficiently thick to maintain the form of the woman's cavity formed by the missing breast while forward wall or second skin 53 remains soft and lifelike.

STEP 13

Hole 54 is ready to be sealed, using the following method:

A 30 mil sheet of clear silicone rubber, such as 375 SWS, is cured in an oven in accordance with specification. Another 30 mil sheet of clear silicone rubber, however, uncured, is placed on top of the cured sheet. A third sheet of polyethylene is placed on top of the uncured sheet to protect it. These sheets, which are referred to as a large patch are then cut to exceed the size of hole 54, shown in FIG. 8. A small button is made consisting of one layer of cured rubber, two layers of mesh, and two layers of uncured rubber with an added layer of polyethylene (for protection of the uncured rubber layers). A small patch is also made consisting of a 30 mil sheet of uncured rubber with polyethylene layers placed on both sides for protection. The relative sizes of large patch 56, small patch 55 and button 57 can be seen in FIG. 2.

The "large" patch, small patch, and button are now ready to be glued together in the following manner. The polyethylene is removed from the button. Button 57 is placed, with its uncured side, in the center of the cured side of large patch 56. The polyethylene layers are removed from the small patch, thus exposing the uncured rubber. The polyethylene layer is also removed from the large patch, thus exposing the uncured rubber. Small patch 55 is then placed in the center of large patch 56 as shown in FIG. 2.

Using a needle to hold onto button 57 and patches 55 and 56, they are placed inside the chamber of prosthesis 60, as shown in FIG. 2. The uncured side of large patch 56 is placed, as shown, abutting first skin 49, thus causing patch 56 to adhere to skin 49. The form is then placed in an oven at 300° F. for 30 minutes, allowing vulcanization to occur. The seal is now permanent, with button 57 acting as a stop valve, similar to a stop valve found in a football.

STEP 14

After button 57 has been placed in position and cured, prosthesis 60 is ready for filling. Silicone gel is inserted through button 57, shown in FIG. 2, with a large syringe. The silicone gel may be 619 GE, SWS V114 or other gels, such as surgical gels made by Dow Corning. Button 57 acts as a stop valve and prevents gel from escaping the inner walls of prosthesis 60.

It will be understood that fill may be added or removed as desired by use of a hypodermic needle inserted through button 57. This is particularly important if the wearer loses or gains weight. Such adding or removing is preferably performed by the maker of the unit.

As prosthesis 60 is being filled, it is placed so that the backwall 48 is tilted 45° with respect to vertical. The prosthesis is also cured in that position in an oven at 300° F. and for a minimum of six hours. By curing the gel in this position, gel filler 70 has a tendency to return to the same position in which it was cured. Consequently, regardless of the type of bra the wearer puts on, or how she handles the bra, prosthesis 60 will always return to its original shape and form.

As previously described, negative body cast 10 is made of an unsupported breast and clay breast 31 is made to correspond with positive cast (unsupported) breast 11a. However, it will be understood that modeled clay breast may be modeled in clay to represent a bra supported breast according to the eye of the sculptor.

In a bilateral mastectomy, the foregoing method steps may also be followed to produce a bilateral prosthesis with the following changes. Since both breasts have been removed, it would be necessary to model two clay breasts 31 on positive body cast 30. It will be understood that the breasts may be modeled as desired by the wearer and the sculptor.

What is claimed is:

1. A method for making a breast prosthesis comprising:
   (a) forming a negative body cast of the body area comprising at least the missing breast;
   (b) forming a positive cast from the negative cast and modeling a breast on the positive cast in the area of the missing breast;
   (c) forming a negative mold over the modeled breast and adjacent portion of the positive body cast;
   (d) removing the negative mold and modeled breast from the positive body cast;
   (e) forming a back wall for the negative mold which conforms to the posterior contours of the modeled breast derived from the positive body cast;
   (f) removing the back wall and the modeled breast from the negative mold and replacing the back wall to form a first cavity defined by the negative mold and back wall;
   (g) filling the first cavity with a curable resin and curing the resin to form a heat-resistant mandrel conforming to the interior contours of said first cavity;
   (h) removing the mandrel from the first cavity;
   (i) coating the mandrel with a film-forming heat-curable silicone resin and curing the film-forming resin to form a shaped first skin on the mandrel;
   (j) shaping a rear wall to the portion of the mandrel defining the posterior contours of the breast and bonding the shaped rear wall to the first skin;
   (k) applying to the first skin a transparent film-forming resin and curing the applied resin to form a transparent protective second skin over the first skin;
   (m) removing the mandrel from the shaped material through an aperture formed in the rear wall to form a second cavity defined by the first and second skins and rear wall;
   (n) sealing the aperture in the rear wall; and
   (o) filling this second cavity with a flexible material to complete the breast prosthesis.

2. The invention of claim 1, wherein the negative mold formed in step (c) is a flexible mold upon which a support casting is formed prior to removal of the negative mold and modeled breast from the positive body cast in step (d).

3. The invention of claim 2, wherein the back wall of the negative mold is formed by disposing a retaining wall on the support cast around the periphery of the posterior portion of the molded breast to define the perimeter of the back wall and filling the space defined by the retaining wall with a curable liquid resin.

4. The invention of claim 1, wherein the mandrel is coated in step (i) with a film-forming silicone resin curable at a temperature of at least about 300° F.

5. The invention of claim 4, wherein the first cavity is filled in step (g) with a fiberglass-reinforced curable resin and cured by action of a catalyst to form a mandrel resistant to temperatures of at least about 300° F.

6. The invention of claim 4, wherein the film-forming heat-curable silicone resin forming the first skin is flesh-colored.

7. The invention of claim 6, wherein the transparent film-forming resin applied to the first skin in step (k) is a clear liquid dispersion of silicone rubber.

8. The invention of claim 7, wherein the second cavity is filled in step (o) with a flexible material comprising a silicone gel.

9. The invention of claim 3, wherein the space defined by the retaining wall is filled with a curable liquid resin comprising a silicone rubber.

10. The invention of claim 5, wherein the rear wall in step (j) is shaped from raw rubber and is cured and bonded to the first skin by vulcanization.

11. The invention of claim 10, wherein a heat-resistant polyester backing is provided for the raw rubber to maintain its shape during vulcanization and wherein the backing is removed after vulcanization.

12. The method of claim 1, wherein after the rear wall is bonded to the first skin in step (j), a silicone rubber material is applied between the top edge of the first skin and the adjacent portion of the rear wall and shaped to form a smooth transition therebetween.

* * * * *